United States Patent [19]

Tomoff et al.

[11] 4,406,541

[45] Sep. 27, 1983

[54] ASSEMBLY USEFUL WITH AN ATOMIC SPECTROMETER

[75] Inventors: Toma Tomoff, Uberlingen; Rolf Tamm, Salem; Bernhard Huber, Uberlingen, all of Fed. Rep. of Germany; Alan Walsh, Brighton, Australia

[73] Assignees: The Perkin-Elmer Corp., Norwalk, Conn.; Bodenseewerk Perkin-Elmer & Co., GmbH, Uberlingen, Fed. Rep. of Germany

[21] Appl. No.: 217,265

[22] Filed: Dec. 11, 1980

[30] Foreign Application Priority Data

Dec. 13, 1979 [DE] Fed. Rep. of Germany ....... 2950105

[51] Int. Cl.³ ..................... G01N 21/72; G01N 21/74
[52] U.S. Cl. ..................................... 356/312; 356/315
[58] Field of Search ................. 356/73, 311, 312, 315, 356/316, 244, 246, 323–325, 432, 434

[56] References Cited

U.S. PATENT DOCUMENTS

| 2,551,833 | 5/1951 | Ewing .................................. 356/323 |
| 3,186,705 | 6/1965 | Rodder .......................... 356/244 X |
| 3,853,407 | 10/1974 | Dewey, Jr. ...................... 356/434 X |
| 4,008,963 | 2/1977 | Huber et al. ........................ 356/312 |
| 4,138,215 | 2/1979 | Huber .................................... 422/58 |
| 4,176,956 | 12/1979 | Temoff et al. ...................... 356/312 |
| 4,176,957 | 12/1979 | Maeda et al. ................... 356/325 X |
| 4,208,372 | 6/1980 | Huber ................................... 422/65 |

FOREIGN PATENT DOCUMENTS

| 55-63743 | 5/1980 | Japan .................................. 356/312 |
| 55-113941 | 9/1980 | Japan .................................. 356/312 |

OTHER PUBLICATIONS

Magyar et al, *GIT Fachz. Lab.* 22, 9/78, pp. 756–758, 761 and 762.
Ashley, *Developments in Applied Spectroscopy*, vol. 1, 1962, pp. 175–185.
Jarrell–Ash Atomic Absorption/Flame Spectrometer Catalog 82-362, Sep. 1964.

*Primary Examiner*—F. L. Evans
*Attorney, Agent, or Firm*—S. A. Giarratana; F. L. Masselle; R. A. Hays

[57] ABSTRACT

A chamber useful with an atomic absorption spectrometer includes at least two atomization means installed therein. The means can be serially aligned with the measuring beam or arranged parallel to the axis thereof.

2 Claims, 6 Drawing Figures

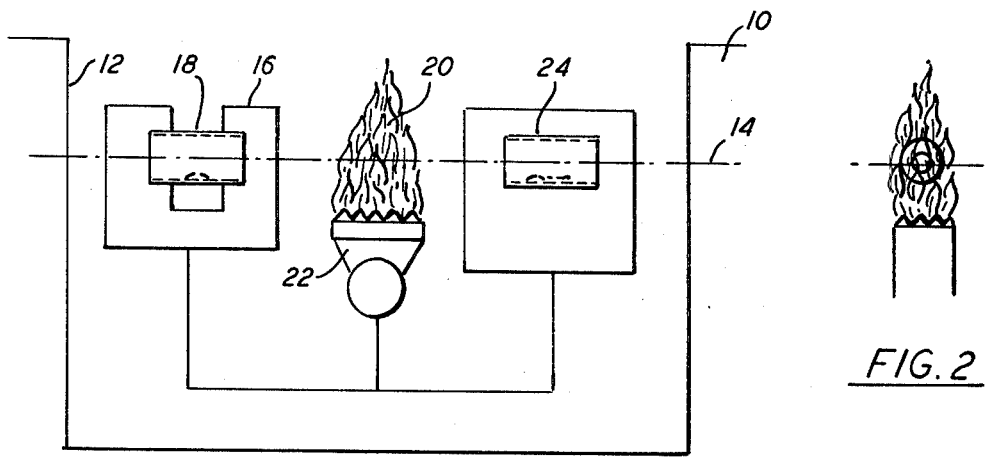
FIG. 1
FIG. 2
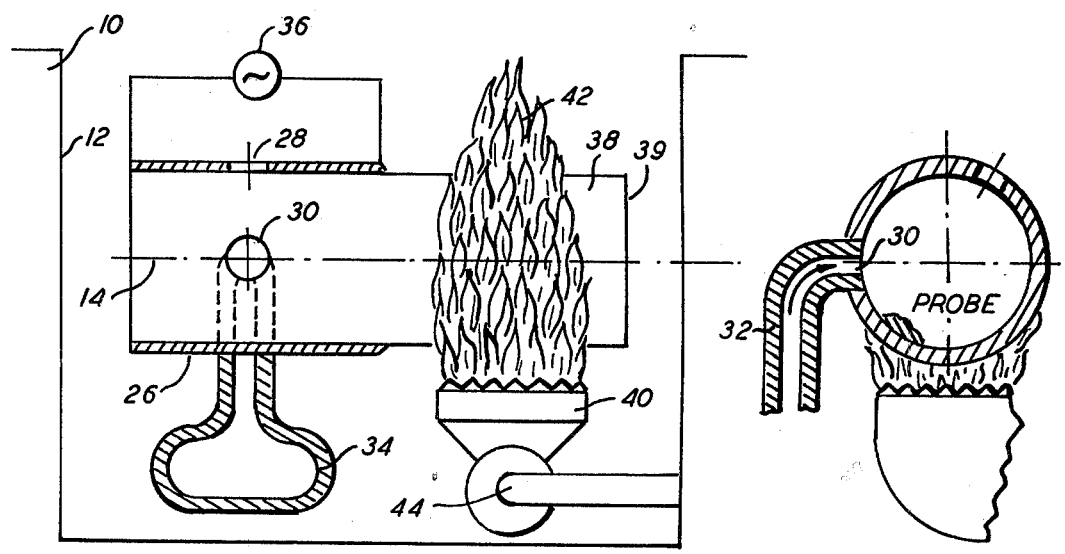
FIG. 3
FIG. 4

ASSEMBLY USEFUL WITH AN ATOMIC SPECTROMETER

BACKGROUND OF THE INVENTION

The present invention generally relates to an atomic absorption spectrometer having a chamber through which passes a measuring beam and in which an atomization means is disposed and, in particular, relates to such a chamber wherein the atomization means provided is selectable.

Conventionally, an atomic spectrometer is used to determine the concentration of an element being sought in a sample. For this purpose, an atomization means is provided for producing an "atom cloud" in which the constituents of the sample are present in an atomic state. A measuring beam, having a light spectrum the same as the absorption spectrum of the element being sought, is directed through the atom cloud and the absorption thereof in the atom cloud is measured. The amount of absorption is representative of the concentration of the element being sought in the sample.

Various atomization means, i.e. means which convert the sample into an atomic condition, are known for such purposes. One such atomization means is a burner wherein the sample is sprayed into the fuel gas-air mixture thereof. The constituents of the sample are decomposed in the flame so that the elements are present in atomic form in the flame.

Another technique employed in atomic absorption spectroscopy is generally known as "flameless atomic absorption spectroscopy". An example of an atomization means for flameless atomic absorption spectroscopy is the conventional graphite tube cell. As well dnown, a graphite tube cell includes a graphite tube positioned between a pair of electrodes. After a sample is introduced into the graphite tube an electrical current is passed, via the electrodes, through the graphite tube so that the graphite tube is heated to high temperatures. In various steps, the sample is dryed, incinerated, and finally atomized, thus forming the "atom cloud" within the graphite tube. In this technique the measuring beam is directed in the longitudinal direction through the graphite tube and the associated annular electrodes. An example of a graphite tube cell of this kind is described in U.S. Pat. No. 4,176,956.

Additionally, it is known that for hydride-forming elements in the sample to be made available to atomic absorption measurement suitable reagents are added to a sample fluid. As a result, a volatile hydride of the element being sought is formed and driven out of the sample. The volatile hydride is then conveyed, usually via a protective carrier gas, into a heated measuring cuvette in which the hydride is decomposed, This decomposition causes the element being sought to be converted in the measuring cuvette into its atomic state, i.e. in the form of an atom cloud through which the measuring beam passes. Examples of such means for the formation of a hydride are described in U.S. Pat. No. 4,183,215 and U.S. Pat. No. 4,208,372.

In any event, substituting one type of atomization means for another is a complicated procedure. For example, the atomization means must be installed and adjusted. In addition, connectors for the supply of current and/or cooling fluid and/or protective gas must also be installed. Generally, the time required for such conversion operations is often relatively long if samples are to be investigated by different methods.

SUMMARY OF THE INVENTION

In view of the foregoing, one object of the present invention is to provide an atomic absorption spectrometer with means for atomizing a sample by different methods without prolonged expensive conversion.

This object is primarily achieved by the use of an assembly, including at least two of the above-mentioned atomization means, arranged such that the measuring beam can be selectively passed through a respective atomization means.

Other objects and advantages will become apparent from the following detailed specification and drawing.

BRIEF DESCRIPTION OF THE DRAWING

Various embodiments of the present invention are described with reference to the drawing in which:

FIG. 1 is a diagrammatic view of a chamber of an atomic absorption spectrometer including an assembly, not drawn to scale, embodying the principles of the present invention.

FIG. 2 is a related view of the spectrometer shown in FIG. 1 as viewed from the direction of the measuring beam;

FIG. 3 depicts another chamber of an atomic absorption spectrometer including another assembly also embodying the principles of the present invention.

FIG. 4 shows a related view of the assembly shown in FIG. 3 as viewed from the direction of the measuring beam;

DETAILED DESCRIPTION OF THE INVENTION

Figure 5:
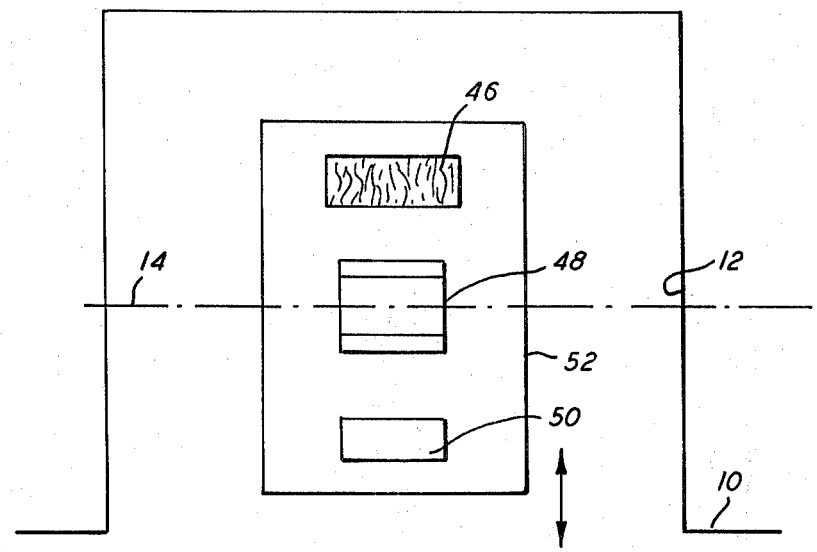
FIG. 5 shows a plan view of a chamber of an atomic absorption spectrometer having yet another assembly, which assembly is fixedly installed on a slider and can be selectively moved into the path of the measuring beam.

In the embodiment shown in FIG. 1, an atomic absorption spectrometer 10 includes a chamber 12 through which passes a measuring beam 14. Disposed in the chamber 12 and arranged successively in the path of the measuring beam 14 are a graphite tube cell 16 having a graphite tube 18, the flame region 20 of a burner 22 and a hyride measuring cuvette 24. In this embodiment, the respective atomization means, 16, 20 or 24, is selected by operating only the desired respective atomization means while the measuring beam 14 is passed unaffected through the other atomization means. In the embodiment shown in FIGS. 3 and 4, the graphite tube 26 of a graphite tube cell, which is arranged in the path of the measuring beam 14, is connected to a sample opening 28, for introducing a fluid or solid sample to be atomized, and to a connection 30. The connection 30 is accomplished via a protective gas outlet line 32 to a means 34 wherein volatile hydrides of a constituent of a sample, which is to be sought, can be produced by the addition of a reagent to the sample. Operationally, the graphite tube 26 can be heated in a conventional manner, i.e. by passing an elctric current from a power supply 36 therethrough. Thus, the graphite tube 26 can be used simultaneously with a hydride measuring cuvette in which volatile hydrides are decomposed.

As shown in FIG. 3 this embodiment of the graphite tube 26 preferably has a continuous slot 38 extending, in a vertical plane proximate one end 39 thereof, over a part of its length. Preferably, a burner 40 is so disposed that the flame 42 thereof extends through the slot 38 into the measuring beam 14 which passes longitudinally through the graphite tube 26. In one mode of operation, sample material is sprayed, via a sprayer 44, into the fuel-air mixture supplied to the burner 40. The opening 28 for introducing the sample and the connection 30 for the hydrides are provided in the non-slotted part of the graphite tube 26.

Figure 6:
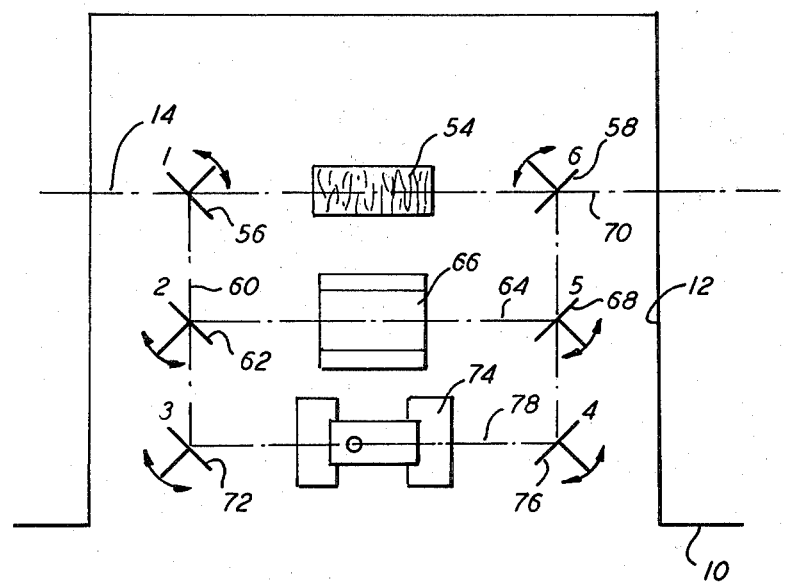
FIG. 6 is a plan view of a chamber of an atomic absorption spectrometer having still another assembly which is also fixedly installed, but wherein the measuring beam can be selectively passed through a respective one of the atomization means.

In the embodiments shown in FIGS. 5 and 6, there are at least two different atomization means (in the specific example shown there are three such means) which are arranged adjacent each other with respect to the respective irradiation direction in the chamber 12. Means are provided for passing the measuring beam 14 through a respective one of the atomization means. Preferably, although not necessarily, the irradiation directions for the atomization means are parallel to the axis of the measuring beam 14 entering the chamber 12.

In the embodiment shown in FIG. 5, the atomization means, including a burner 46, a hydride measuring cuvette 48 and a graphite tube cell 50 are arranged on a slider or carriage 52 which is transversely displaceable with respect to the axis of the measuring beam 14. Hence, any one of the atomization means 46, 48 and 50 can be selectively positioned in the path of the measuring beam 14.

In the embodiment shown in FIG. 6, a first atomization means, for example, a burner 54, is positioned in the path of the measuring beam 14 passing directly through the chamber 12. Mirrors 56 and 58 are arranged on both sides, i.e. in front of and behind, the burner 54 and adapted so as to be pivotable into the path of the measuring beam 14, to deflect the measuring beam 14 90° in the horizontal plane therof. In addition, in the path 60 of the deflected beam, i.e. deflected from the front of the burner 54, is a mirror 66 which is adapted so as to deflect the path 60 of the deflected beam 60 through 90°. Thus, the second deflected path 64 passes the beam through a second atomization means 66, in this embodiment a hydride measuring cuvette 66. To the rear of the second atomization means 66 another mirror 68 is provided for deflecting the beam 63 to the mirror 58 positioned behind the first atomization means 54 which is adapted to deflect the beam in the direction of a non-deflected beam 70.

The mirrors 62 and 68 which are preferably arranged in front of and to the rear of, respectively, the second atomization means 66 and, in this embodiment, are adapted so as to be pivotable out of the path of the deflected beam 60 and 64, respectively. Arranged in the path of the deflected beam 60, which is undeflected when mirror 62 is pivoted out of the path of the beam 60, a further mirror 72 is disposed which also deflects the deflected beam 60 through 90° in the horizontal plane and thus passes the beam through a third atomization means 74, in this instance a graphite tube cell. Disposed to the rear of the third atomization means 74 a further mirror 76 is provdied for deflecting the beam 78, after it has passed through the third atomization means 74, past the mirror 68 provided behind the second atomization means 66 and which has been pivoted out of its operative position, onto the mirror 58 which is arranged behind the first atomization means thereby deflecting the beam in the direction of the non-deflected beam 70.

Although specific exemplary embodiments have been shown and described it will be obvious to those skilled in the art that various modifications can be made without departing from the spirit and scope of the present invention. The present invention is therefore limited only by the appended claims and the reasonable interpretation therof.

What is claimed is:

1. An assembly for use in an atomic absorption spectrometer having a chamber through which passes a measuring beam and in which an atomization means is disposed, said assembly comprising:

at least two atomization means fixedly installed in said chamber;

said atomization means includes a graphite tube, said tube being disposed in the path of said measuring beam, and having a sample opening for introducing a sample to be atomized, said opening connecting to a means for generating volatile hydrides of a consituent of said sample, said hydrides so generated being passed into said tube through said opening connection by a protective gas flow whereby said graphite tube is operable as a hydride measuring cuvette; said tube also including a continuous slot in a vertical plane, said slot being proximate one end of said graphite tube and extending over a part of the length thereof, said opening for introducing said sample and said connection for said hydrides being provided in the non-slotted part of said graphite tube;

a burner positioned such that the flame therof extends into said slot whereby said measuring beam passes therethrough; and means for passing a heating current through said non-slotted part of said graphite tube.

2. An assembly as claimed in claim 1 wherein said atomization means are successively aligned in the path of said measuring beam.

* * * * *